(12) United States Patent
Doerr

(10) Patent No.: US 8,509,921 B2
(45) Date of Patent: Aug. 13, 2013

(54) IMPLANTABLE ELECTRODE LINE OR ELECTRODE LINE CONFIGURATION

(75) Inventor: Thomas Doerr, Berlin (DE)

(73) Assignee: BIOTRONIK CRM Patent AG (CH)

( * ) Notice: Subject to any disclaimer, the term of this patent is extended or adjusted under 35 U.S.C. 154(b) by 575 days.

(21) Appl. No.: 12/493,264

(22) Filed: Jun. 29, 2009

(65) Prior Publication Data

US 2010/0010607 A1    Jan. 14, 2010

(30) Foreign Application Priority Data

Jul. 10, 2008   (DE) .......................... 10 2008 040 304

(51) Int. Cl.
*A61N 1/00*    (2006.01)
(52) U.S. Cl.
USPC ........................................................ 607/122
(58) Field of Classification Search
USPC ......................................... 607/122, 123, 126
See application file for complete search history.

(56) References Cited

U.S. PATENT DOCUMENTS

| | | | | |
|---|---|---|---|---|
| 4,836,204 A * | 6/1989 | Landymore et al. | .......... | 606/215 |
| 5,728,140 A | 3/1998 | Salo et al. | | |
| 5,976,174 A * | 11/1999 | Ruiz | ............................ | 606/213 |
| 6,270,515 B1 * | 8/2001 | Linden et al. | ................. | 606/213 |
| 6,312,446 B1 * | 11/2001 | Huebsch et al. | ............. | 606/213 |
| 6,478,776 B1 * | 11/2002 | Rosenman et al. | ...... | 604/164.01 |
| 6,645,143 B2 * | 11/2003 | VanTassel et al. | ............ | 600/300 |
| 7,229,415 B2 * | 6/2007 | Schwartz | ...................... | 600/486 |
| 7,515,970 B2 * | 4/2009 | Zhang et al. | ................... | 607/126 |
| 7,657,324 B2 * | 2/2010 | Westlund et al. | ............. | 607/122 |
| 7,840,266 B2 * | 11/2010 | Libbus et al. | ..................... | 607/9 |
| 7,840,281 B2 * | 11/2010 | Kveen et al. | ................... | 607/126 |
| 8,244,377 B1 * | 8/2012 | Pianca et al. | ................... | 607/126 |
| 2005/0085883 A1 | 4/2005 | Ollivier et al. | | |
| 2006/0224224 A1 | 10/2006 | Muhlenberger et al. | | |
| 2008/0046059 A1 * | 2/2008 | Zarembo et al. | ............. | 607/122 |
| 2008/0046060 A1 * | 2/2008 | Kroll et al. | ..................... | 607/122 |
| 2008/0082132 A1 * | 4/2008 | Annest et al. | ..................... | 607/4 |
| 2008/0294177 A1 * | 11/2008 | To et al. | ......................... | 606/139 |
| 2009/0036961 A1 * | 2/2009 | Chong et al. | ................... | 607/122 |
| 2009/0318989 A1 * | 12/2009 | Tomaschko et al. | ............. | 607/9 |
| 2010/0016864 A1 * | 1/2010 | Drake et al. | ................... | 606/129 |
| 2010/0069983 A1 | 3/2010 | Peacock, III et al. | | |

FOREIGN PATENT DOCUMENTS

| | | |
|---|---|---|
| EP | 1516644 A1 | 3/2005 |
| WO | WO 2006105395 A2 | 10/2006 |
| WO | WO 2008058265 A2 | 5/2008 |

OTHER PUBLICATIONS

European Search Report (09162536.8) Sep. 17, 2010.

* cited by examiner

*Primary Examiner* — George Manuel
*Assistant Examiner* — Minh Duc Pham
(74) *Attorney, Agent, or Firm* — Craig A. Fieschko, Esq.; DeWitt Ross & Stevens S.C.

(57) ABSTRACT

An implantable line, in particular an electrode line and/or sensor line and/or medicine supply line for implantation in the left ventricle of the heart with perforation of the atrial or ventricular septum, includes an elongated flexible line body, an electrode and/or a sensor and/or a medicine administering device at or near the distal end of the line body, and a closure element integrally molded on the line body or connected thereto for sealing the perforation site in the septum.

20 Claims, 7 Drawing Sheets

IMPLANTABLE ELECTRODE LINE OR ELECTRODE LINE CONFIGURATION

FIELD OF THE INVENTION

Figure 1:
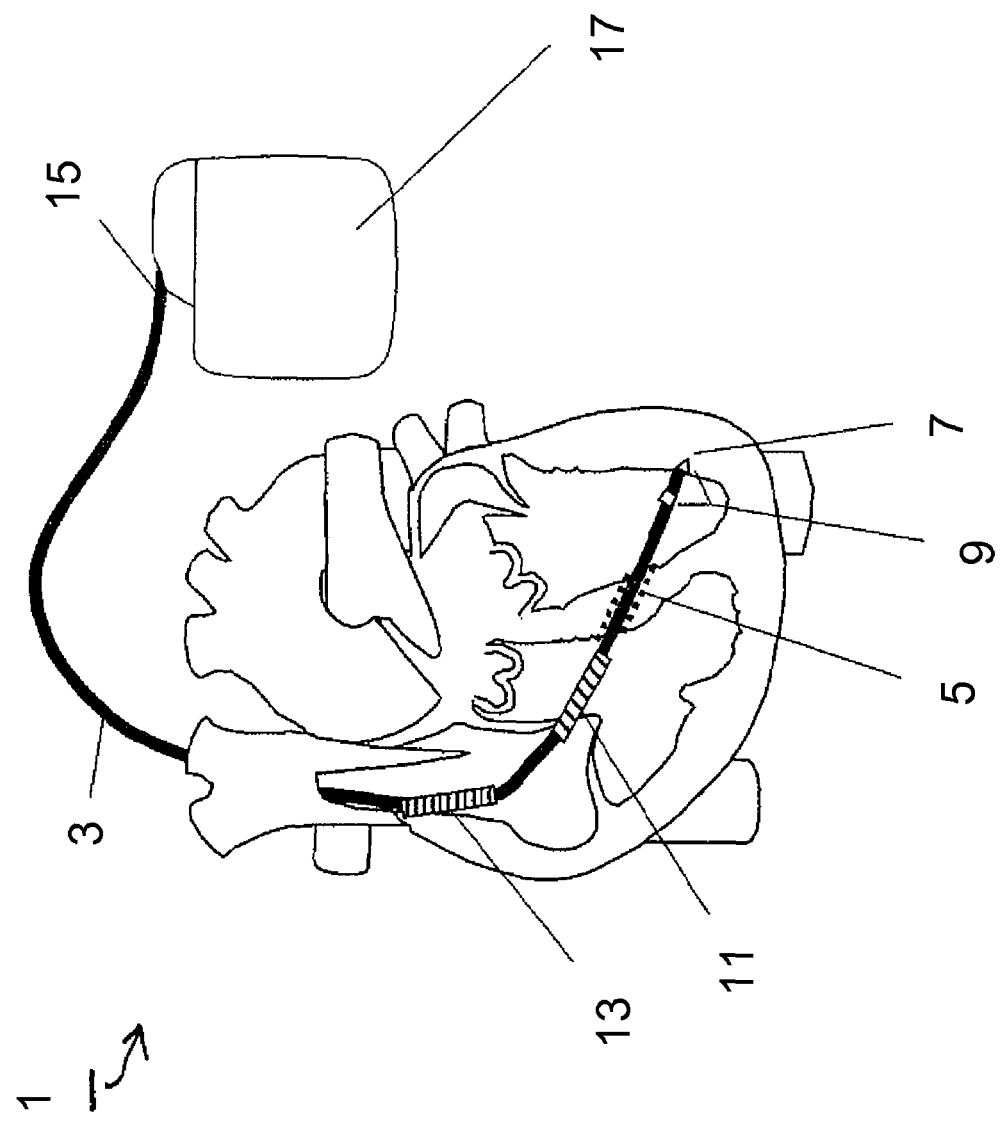

The invention relates to an implantable line or line configuration for implantation in the left ventricle of the heart with perforation of the atrial or ventricular septum.

BACKGROUND OF THE INVENTION

Implantation of an electrode in a left-ventricular vein via the coronary sinus is currently considered to be a state-of-the-art procedure for left-ventricular stimulation and detection. These so-called coronary sinus electrodes are used primarily for cardiac resynchronization therapy.

The medical literature contains a growing number of case reports of transseptal implantation of left-ventricular stimulation electrodes for resynchronization therapy. These implantation techniques have always been implemented with the help of existing catheters, guide wires and electrodes. Puncture of either the atrial septum or the ventricular septum has been described for access to the left ventricle. See, for example, Transseptal Endocardial Left-Ventricular Pacing: An Alternative Technique for Coronary Sinus Lead Placement in Cardiac Resynchronization Therapy, B. M. van Gelder, M. G. Scheffer, A. Meijer, et al., *Heart Rhythm* April 2007: 4(4):454-60.

Furthermore, concepts for transmural left-ventricular pressure measurement are also currently being investigated in clinical trials wherein pressure sensors are placed transmurally in the left ventricle for permanent telemetric pressure monitoring in the left ventricle. See, e.g., www.transomamedical.com or the following technical publications:

A Novel Technique for Assessing Load-Dependent Cardiac Function During LVAD Support Using Telemetered Left-Ventricular Pressure. P. 1. McConnell, C. L. Del Rio, P. Kwiatkowski, D. Farrar, T. Shipkowitz, R. E. Michier, B. Sun, *ASAIO Journal* 51(2): 31A, March/April 2005;

In-Vivo Safety and Accuracy of a Clinically Applicable Telemetered Left-Ventricular Pressure Module: Intermediate-Term Results, P. I. McConnell, D. de Cunha, T. Shipkowitz, J. Van Hee, P. Long and R. Hamlin, *Heart Failure Society Meeting*, September 2004;

A System for Long-Term Measurement of Left-Ventricular Pressure in Heart Failure Patients Living at Home, N. Sweitzer, S. Park, *Heart Failure Society Meeting*, September 2002;

Automated Non-Invasive Monitoring of Left-Ventricular Hemodynamics During Onset of Heart Failure in an Ambulatory Yucatan Mini Pig Model Using a New System Under Development for Assessing Heart Failure Patients at Home, S. Park, N. Sweitzer, *Heart Failure Society Meeting*, September 2002; or A System for Long-Term Measurement of Left-Ventricular Pressure in Heart Failure Patients Living at Home, S. Park, N. Sweitzer and G. May, *Heart Failure & Circulatory Support Summit*, Cleveland, Ohio, August 2002.

A number of commercial closure systems are currently available for congenital atrial septal defects, open foramen or foramen ovale and ventricular septum defects (e.g., Premere™ PFO, SJM), which can be positioned via catheter techniques and which ensure a reliable closure of the septum defect. In this regard, see Transcatheter Patent Foramen Ovale Closure Using the Premere PFO Occlusion System, Andrea Donti, Alessandro Giardini, Luisa Salomone, Roberto Formigari, Fernando M. Picchio, *Catheterization and Cardiovascular Interventions*, vol. 68/5 2006.

WO 2006/105395 A2 describes a transseptal/transmyocardial ventricular stimulation electrode.

In approximately 10-15% of the implantations, anatomical conditions prohibit reliable implantation of a left-ventricular coronary sinus electrode. Furthermore, the incidence of dislocation of left-ventricular electrodes implanted for cardiac resynchronization therapy (CRT) by way of the coronary sinus is greater than that with a traditional right-ventricular pacemaker electrode. For these reasons, purely left-ventricular stimulation using a coronary sinus electrode is not currently being used for treatment of bradycardia or for implantation of automatic cardioverter/defibrillators (ICD), because neither the success nor the safety of implantation is guaranteed with this type of left-ventricular electrode. The very limited options for placement are another disadvantage of a coronary sinus electrode. In most cases, there are only one or two different positions for attachment of the probe. This is discussed as one of the primary causes of the poor responder rate (60-70%) of CRT at the present time.

The techniques presented above for electrode implantation in the left ventricle via the atrial or ventricular septum are very complex and have not yet been successful because of the risks (RV shunt, thrombi). Free placement of the electrode in the left ventricle is possible here, and this would eliminate the disadvantages of attachment of the probe, the responder rate, and anatomical restrictions.

Transluminal LV pressure measurement can be used for a system to permanently penetrate through the myocardium into the left ventricle. This introduces a very short probe into the left ventricle which has a pressure sensor and is of the type that cannot be used for electric stimulation of the heart. However, the probe described in WO 2006/105395 A2 is designed so that the active stimulation area lies only in the area of the left-ventricular septum and cannot be positioned freely in the left ventricle. In addition, WO 2006/105395 A2 does not discuss repositioning or the explantation ability of an electrode.

SUMMARY OF THE INVENTION

To reduce the aforementioned disadvantages, an object of the present invention is to construct a left-ventricular probe that can be advanced from the right ventricle into the left ventricle through the atrial or ventricular septum, and which can be maneuvered freely and secured within the left ventricle, whereby the risk of implantation of a left-right shunt is is minimized through suitable design measures on the probe body. Furthermore, the possibility of repositioning such a probe and its explantation can be taken into account.

This object is achieved by implantable lines and/or line configurations as defined by the accompanying claims.

The invention provides a suitable element at the perforation site in the atrial or ventricular septum through which the electrode line is inserted, said line ensuring a reliable mutual seal of the areas of the heart adjacent to the septum, at least during the ingrowth phase. This can be accomplished by the electrode line itself, which then carries a suitable closure element. In other versions of the invention, a separate closure element is provided for this purpose, with the closure element being positioned before the insertion of the electrode line in the septum and then being punctured by the insertion of the electrode line.

It is noted that the invention can also be used with a line and/or line configuration provided for use in the left atrium if the line is passed through the septum into the left atrium.

An advantage of the invention is the secure and reliable access to the left ventricle without the anatomical restrictions of the coronary sinus access. With this technique, it is then possible to provide cardiac pacemakers, ICDs and CRT devices that are controlled primarily via the left ventricle. The advantages of primarily left-controlled systems include:
- physiologically more favorable stimulation site;
- better sensing signals due to the larger muscle mass;
- more favorable conditions for affixing the probe and a lower risk of perforation due to the greater wall thickness;
- better possibilities of hemodynamic optimization by stimulation;
- the disadvantage of RV stimulation is largely eliminated.

In comparison with the known approaches, simple repositioning and explantation of the transseptal probe is also achieved when using the feed-through ("working channel").

The closure body can be fixedly connected to the electrode, so that longitudinal movement of the electrode body in the septum is prevented.

In another version of the invention, the closure body is characterized as an expandable screen.

In a similar version of the invention, the closure body is embodied as a first seal in the form of an expandable screen and as a second seal in the form of an expandable anchor that is displaceable on the electrode (proximally to the screen).

The probe is preferably coated in the area of the closure body to promote rapid development of connective tissue in the area of the perforation site.

The "working channel" preferably has a maximum free diameter of 2 mm when no electrode is pushed through it (acceptable left-right shunt).

In another version of the invention, the "working channel" is characterized by X-ray markers and/or is made of a radiopaque material.

The working channel is attached in the septum, e.g., by expandable fixators (e.g., stents). The LV probe may also be attached in the working channel by expandable fixators. These fixators are attached to the probe. The expandable fixators may also be used for unipolar and bipolar stimulation of the septum.

BRIEF DESCRIPTION OF THE INVENTION

Figure 2:
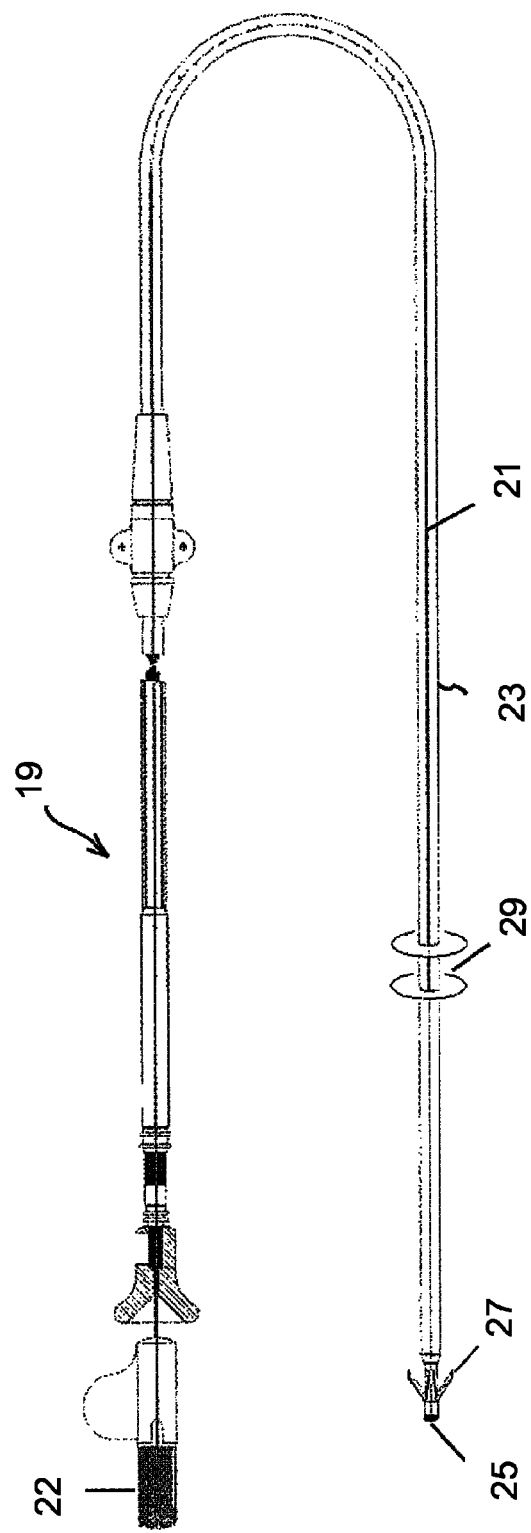
Figure 3:
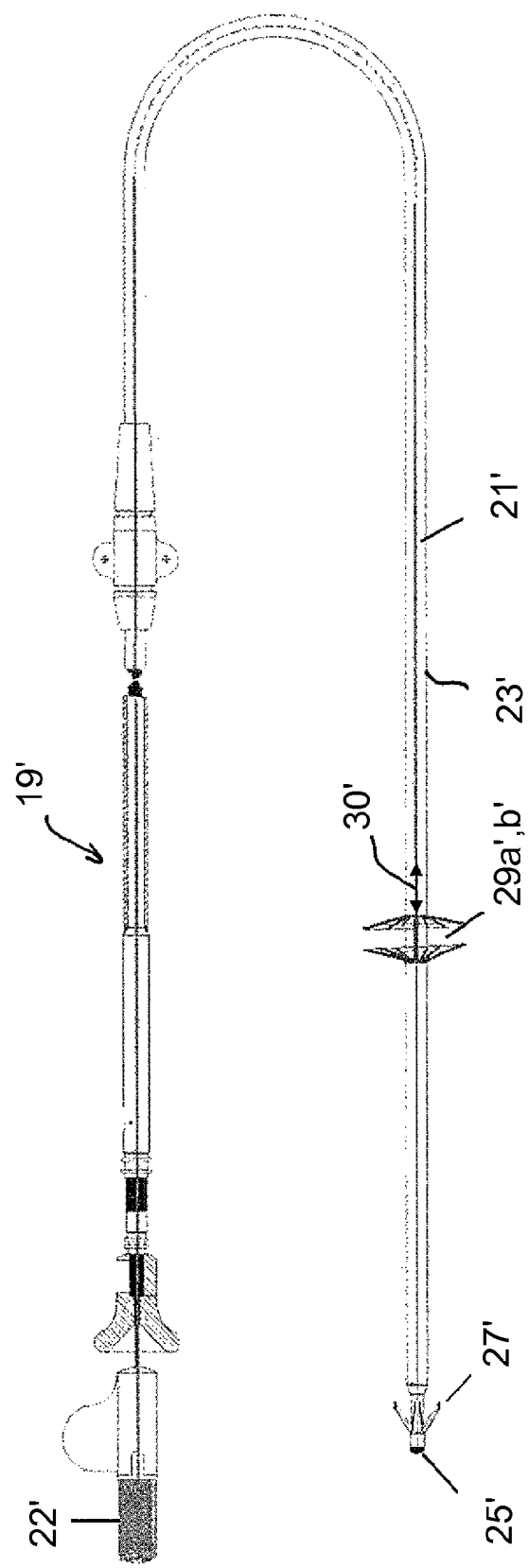
Figure 4A:
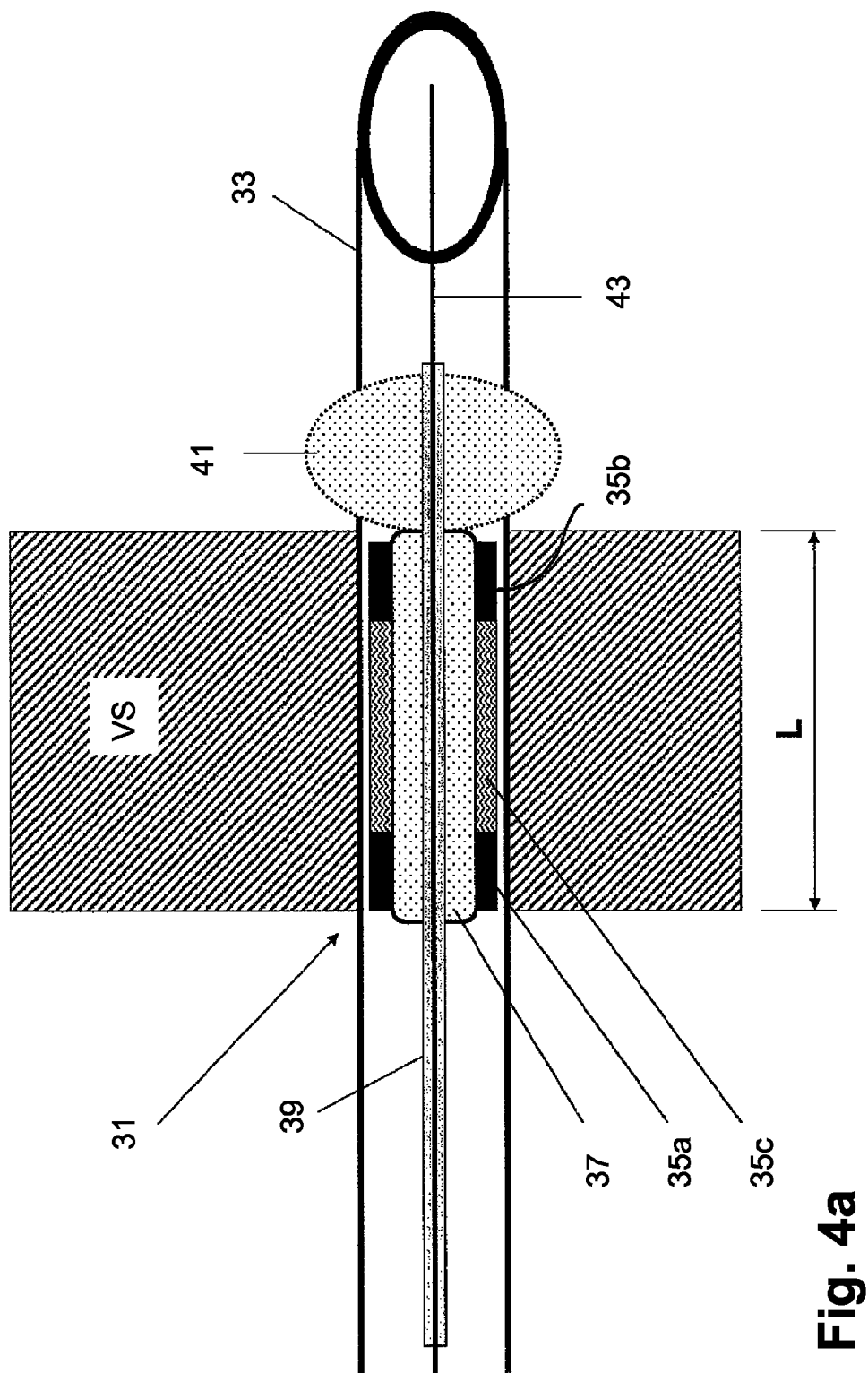
Figure 4B:
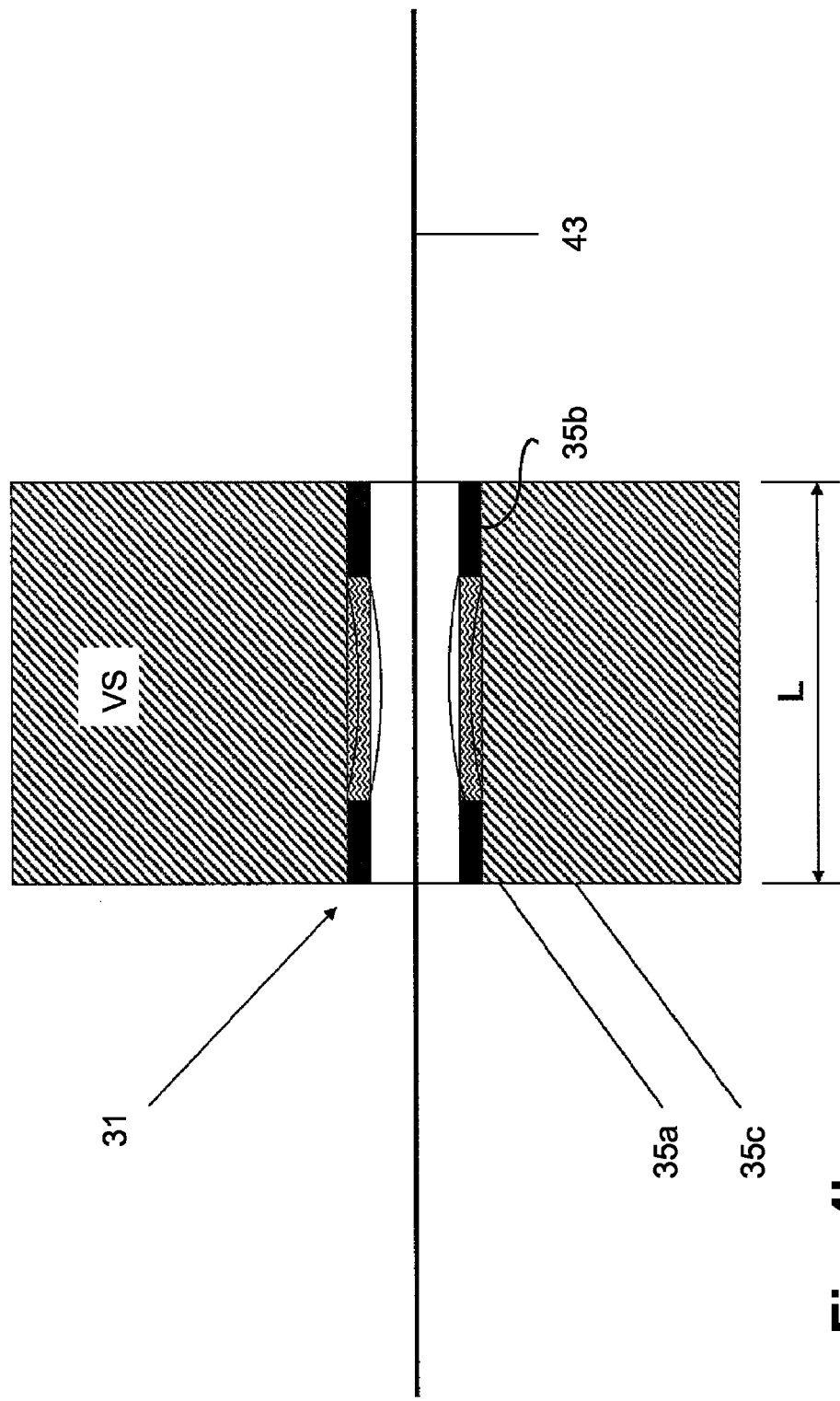
Figure 4C:
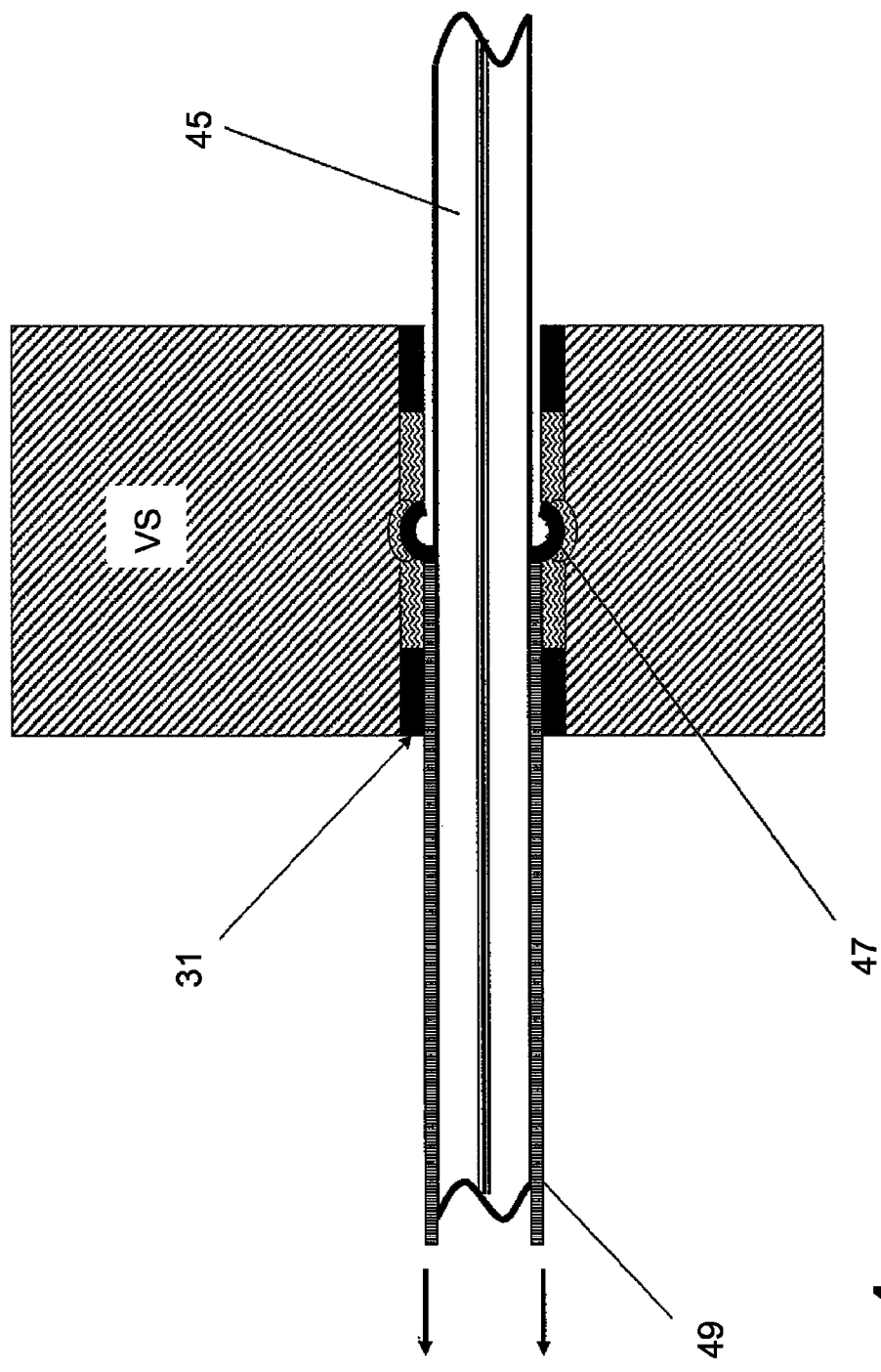
Figure 5:
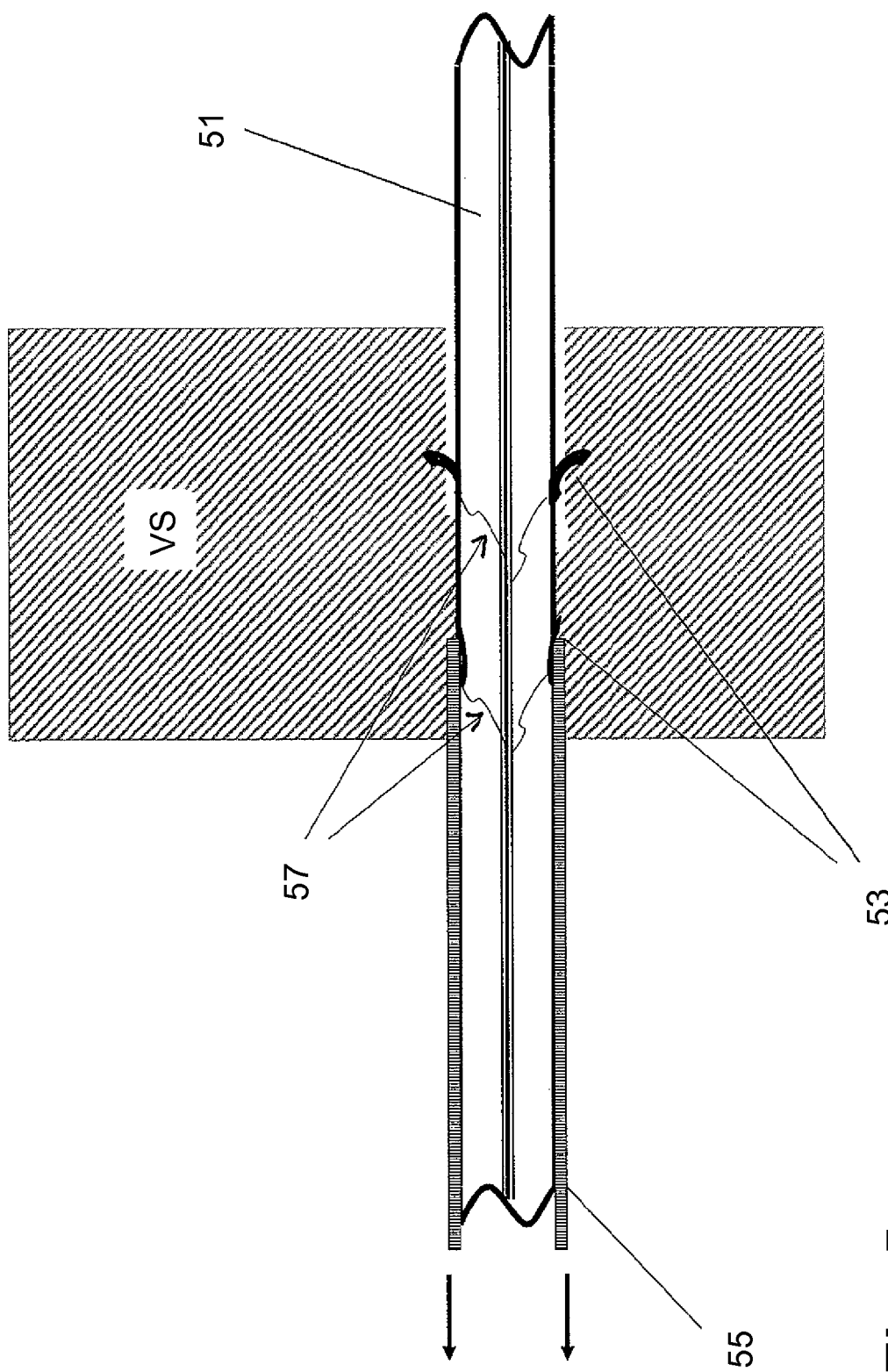

Advantages of the invention will also be apparent from the following description of exemplary versions of the invention and the associated drawings, wherein;

FIG. 1 shows an overall view of a defibrillation configuration with an exemplary version of the invention, FIG. 2 shows an electrode line according to an exemplary of the invention, FIG. 3 shows an electrode line according to an alternative version of the invention, FIGS. 4a to 4c shows diagrams of another version of the invention in various phases of implementation, and FIG. 5 shows a detailed view of another version of the invention.

DETAILED DESCRIPTION OF THE INVENTION

FIG. 1 shows an exemplary version of the invention. 1. A left-ventricular electrode line 3 is advanced through an implantable transseptal feed-through ("working channel") 5 into the left ventricle where it is affixed by means of a conventional screw 7. In the embodiment shown here, the left-ventricular electrode line 3 has a bipolar stimulation electrode 9 and also has two shock electrodes (distal shock electrode 11 and proximal shock electrode 13). The diameter of the distal shock electrode is selected so that it cannot slip through the feed-through into the left ventricle. The line 3 is connected to an electrode plug 15 (e.g., types IS-4 and/or IS-1 and DF-1) with an implantable defibrillator 17.

FIG. 2 shows another version of the invention, specifically an electrode line 19, which can be implanted by means of a guide wire 21 with a proximal handle 22 and whose design is essentially known in this field of technology, including a flexible electrode line body 23 (shown here bent into a U shape), a tip electrode 25, and a distal fixation hook 27 for anchoring in the wall of the ventricle. However, this electrode line 19 includes a new feature in the form of a closure element 29 (represented here symbolically as two disk-like seals with a small distance between them) for closure of a perforation site in the septum through which the electrode line 19 (as shown in FIG. 1) is guided into the left ventricle.

FIG. 3 shows as a specific design of this embodiment an electrode line 19' in which the closure element 29 is formed by two mutually spreadable screens 29a', 29b', which can be spread in opposite directions and, thanks to an additional control wire 30', can be spread on both sides of the perforation site in the septum after insertion of the electrode line 19', and in the spread state, can seal the electrode line 19' from the environment of the puncture site.

The proximal screen may additionally be pushed onto the probe by means of the additional s mandrel 30', so that the ventricular septum is secured between the two screens. The two screens 29a', 29b' may also be used as active (e.g., bipolar) stimulation electrodes.

The septal feed-through ("working channel") 31 shown in FIGS. 4A-C is first created by means of a Brockenbrough needle 33 by puncture of the ventricular septum VS. The feed-through itself consists of two expandable stents 35a, 35b embedded in a flexible biocompatible tubing 35c, e.g., silicone or polyurethane. This feed-through is mounted on an expandable balloon 37 of a balloon catheter 39 and is affixed in the septum by balloon expansion.

To ensure the correct position of the feed-through, a second balloon 41 of a larger diameter is positioned on the balloon catheter, so that the balloon expands after puncture of the left ventricle and retraction of the Brockenbrough needle. Then the balloon catheter is retracted to such an extent that the larger balloon 41 contacts the ventricular septum VS. Next the feed-through 31, the length L of which was determined in advance by echocardiography, is affixed by expansion of the smaller balloon 37 in that the expandable balloon 37 pushes the stents 35a, 35b with the length of tubing 35c between them against the wall of the hole in the septum formed by the Brockenbrough needle.

After removal of the balloon catheter 39, the feed-through 31 and optionally a guide wire 43 remain in the puncture site (FIG. 4B). The two stents 35a, 35b are visible in the X-ray image, so that subsequent navigation of the LV probe through this transseptal feed-through is readily possible. The left-right shunt volume is minimized by the flexible part of the feed-through 31. If no line is inserted, the inside width d is reduced by an inward curvature of the flexible length of tubing 35c between the stents 35a, 35b.

FIG. 4C shows the transseptal feed-through 31 described above together with a left-ventricular line and/or probe 45. To avoid a longitudinal movement of the probe 45 within the transseptal feed-through, it can be attached by a self-expanding fixator 47 within the feed-through. In the exemplary embodiment, this fixator 47 is implemented as a radiopaque spring element, which is released by retraction of a tubing 49, thereby securing the electrode line 45 in the feed-through. This prevents abrasion of the electrode line 45 or the fixator 47.

As an alternative to the LV probes described above in combination with a feed-through, FIG. 5 shows an LV probe which can be attached independently without a separate closure element by means of expanding fixators 53 affixed directly in the septum, such that these s fixators 53 are first sheathed by a tubing 55 and then expanded by retracting this tubing by means of springs 57 in the septum VS.

The tubing 55 is designed so that it can be removed completely from the electrode line 51 after implantation (e.g., by peeling). For the case of explantation of such an electrode line 51, the fixators 53 can be "inserted" again by feeding corresponding tubing over the electrode line 51 and fixators 53 after cutting off the electrode plug. The fixators 53 may be used as active stimulation electrodes by connecting them to the electric feeder lines 57 of the electrode line 51. Implantation in this line is likewise accomplished by using a Brockenbrough needle.

The invention is not limited to the examples described above and the features emphasized here, but instead encompasses all forms and modifications encompassed by the claims below.

What is claimed is:

1. An implantable line for implantation in the left ventricle of the heart with perforation of the atrial or ventricular septum, the implantable line including:
    a. an elongated flexible line body having a distal end, and including at least one of:
        (1) an electrode,
        (2) a sensor, and
        (3) a medicine administering device,
        at or near the distal end,
    b. a closure element on the line body, wherein:
        (1) the closure element seals the perforation site in the septum,
        (2) at least a portion of the closure element has an expandable section having a diameter which expands to be greater than the diameter of adjacent lengths of the line body, and
        (3) the closure element also includes a reducing section adjacent the expandable section, the reducing section having a diameter which is reduced when the diameter of the expandable section is expanded,
    c. a distal fixator:
        (1) spaced from the closure element, and
        (2) at or near the distal end of the line body,
        wherein the fixator is configured to fix the distal end of the line body in or adjacent a wall of the left ventricle away from the septum.

2. The line of claim 1 including two or more stimulation electrodes situated along the line body, wherein stimulation electrodes are situated on opposite sides of the closure element along the line body.

3. The line of claim 1 wherein the closure element includes an anchor displaceable in its entirety along the length of the line body, whereby the anchor may be moved within or into abutment with the septum.

4. The line of claim 3 wherein the anchor defines a stimulation electrode for stimulation of the septum.

5. The line of claim 1 wherein one or more of:
    a. at least a portion of the closure element, and
    b. a section of the line body adjacent the closure element, is coated with a growth-promoting ingredient which promotes rapid development of connective tissue adjacent the coated area.

6. The line of claim 1 wherein the closure element includes a feed-through having opposing open ends, with the line body extending through the open ends of the feed-through.

7. The line of claim 6 wherein the feed-through includes:
    a. an expandable section fit about the outer diameter of the line body, wherein the expandable section is expandable to increase its outer diameter when the closure element is fit within the septum; and
    b. a flexible section:
        (1) adjacent the expandable section, and
        (2) fit about the outer diameter of the line body,
        wherein the flexible section is compressible to reduce its inner diameter when the closure element is fit within the septum.

8. An implantable line for implantation in the left ventricle of the heart with perforation of the atrial or ventricular septum, the implantable line including:
    a. an elongated flexible line body having a distal end, and including at least one of:
        (1) an electrode,
        (2) a sensor, and
        (3) a medicine administering device,
        at or near the distal end,
    b. a closure element on the line body, wherein the closure element
        (1) seals the perforation site in the septum, and
        (2) includes a feed-through having opposing open ends, wherein the feed-through:
            (a) is fit about the outer diameter of the line body and through the perforation site in the septum, and
            (b) includes a section with an inner diameter that reduces upon placement of the feed-through within the septum.

9. The line of claim 8 wherein the feed-through includes at least one section with an outer diameter that increases upon placement of the feed-through within the septum.

10. The line of claim 8 wherein the inner diameter of the feed-through is less than or equal to 2 mm.

11. The line of claim 8 wherein at least a portion of the feed-through bears X-ray marker material.

12. The line of claim 8 wherein the closure element includes an expandable fixator thereon, wherein the expandable fixator expands to extend beyond the outer diameter of the feed-through.

13. The line of claim 12 wherein the fixator defines a stimulation electrode for stimulation of the septum.

14. An implantable line for implantation in the left ventricle of the heart with perforation of the atrial or ventricular septum, the implantable line including an elongated flexible line body having:
    a. a distal end;
    b. a closure element on or about the outer diameter of the line body, wherein:
        (1) at least a portion of the closure element has an outer diameter that expands upon placement of the closure element within the septum, and
        (2) at least a portion of the closure element has an inner diameter that is reduced when the outer diameter is expanded;
    c. an electrode situated between the distal end and the closure element.

15. The implantable line of claim 14 wherein the inner diameter of the closure element is fit about the line body.

16. The implantable line of claim 15 wherein the closure element includes an expandable fixator which expands to an outer diameter greater than the outer diameter of the line body.

17. The implantable line of claim 14 wherein the closure element includes a seal extending about the line body, the seal having:
   a. a seal outer diameter at least twice as great as the outer diameter of the line body, and
   b. a seal length measured along the length of the line body, wherein the seal length is less than the seal outer diameter.

18. An implantable line for implantation in the left ventricle of the heart with perforation of the atrial or ventricular septum, the implantable line including an elongated flexible line body having:
   a. a distal end;
   b. a closure element on or about the outer diameter of the line body, wherein the closure element includes:
      (1) an expandable fixator situated on or about the line body, the fixator:
         i. expanding to extend beyond the outer diameter of the line body,
         ii. including one or more members spring-biased to extend away from the outer diameter of the line body, the members being restrained toward the outer diameter of the line body by tubing retractably fit over the members, and
         iii. including a stent extending about the line body;
      (2) a reducing section having an inner diameter which reduces to closely fit about the outer diameter of the line body;
   c. an electrode situated between the distal end and the closure element.

19. An implantable line for implantation in the left ventricle of the heart with perforation of the atrial or ventricular septum, the implantable line including an elongated flexible line body having:
   a. a distal end;
   b. a closure element on or about the outer diameter of the line body, the closure element including two seals extending about the line body wherein:
      (1) one of the seals is defined by an expandable member situated about the line body, the expandable member expanding to extend beyond the outer diameter of the line body;
      (2) the other of the seals is defined by an anchor displaceable in its entirety along the length of the line body, the anchor having an anchor outer diameter greater than the outer diameter of the line body;
      whereby the seals may be situated on opposite sides of the septum to hold the closure element thereon; and
   c. an electrode situated between the distal end and the closure element.

20. An implantable line for implantation in the left ventricle of the heart with perforation of the atrial or ventricular septum, the implantable line including an elongated flexible line body having:
   a. a proximal end;
   b. an opposing distal end;
   c. a distal fixator at or near the distal end, the fixator including a member configured to engage a wall of the left ventricle away from the septum to engage the distal end thereon;
   d. a closure element spaced from the distal fixator, the closure element being situated on or about the outer diameter of the line body, wherein at least a portion of the closure element:
      (1) has an outer diameter that increases upon placement of the closure element within the septum, and
      (2) has an inner diameter that reduces upon placement of the closure element within the septum, wherein the portion having the reduced inner diameter is adjacent the portion having an increased outer diameter;
   e. a distal therapeutic device situated at or distally to the closure element, the distal therapeutic device including at least one of:
      (1) an electrode,
      (2) a sensor, and
      (3) a medicine administering device;
   f. a proximal therapeutic device situated at or proximally to the closure element, the distal therapeutic device including at least one of:
      (1) an electrode,
      (2) a sensor, and
      (3) a medicine administering device.

* * * * *